(12) United States Patent
Mohamed et al.

(10) Patent No.: US 11,186,493 B2
(45) Date of Patent: Nov. 30, 2021

(54) GREEN SYNTHESIS OF NOBLE METAL/TRANSITION METAL OXIDE NANOCOMPOSITE

(71) Applicant: Imam Abdulrahman Bin Faisal University, Dammam (SA)

(72) Inventors: Hanan Hussein Amin Mohamed, Dammam (SA); Ines Mohsen Hammami, Dammam (SA); Tamer Ezzat Youssef Moustafa, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 159 days.

(21) Appl. No.: 16/561,559

(22) Filed: Sep. 5, 2019

(65) Prior Publication Data
US 2021/0070629 A1 Mar. 11, 2021

(51) Int. Cl.
| | |
|---|---|
| *B22F 9/24* | (2006.01) |
| *C01G 23/08* | (2006.01) |
| *A23F 5/02* | (2006.01) |
| *B82Y 30/00* | (2011.01) |
| *B01J 35/00* | (2006.01) |

(52) U.S. Cl.
CPC ............ *C01G 23/08* (2013.01); *A23F 5/02* (2013.01); *B22F 9/24* (2013.01); *B01J 35/004* (2013.01); *B82Y 30/00* (2013.01); *C01P 2002/72* (2013.01); *C01P 2002/84* (2013.01); *C01P 2004/03* (2013.01); *C01P 2004/04* (2013.01); *C01P 2004/64* (2013.01)

(58) Field of Classification Search
None
See application file for complete search history.

(56) References Cited

U.S. PATENT DOCUMENTS

| | | | |
|---|---|---|---|
| 9,000,017 B2 | 4/2015 | Thys et al. | |
| 9,491,947 B1 * | 11/2016 | Awad | A01N 65/20 |

(Continued)

FOREIGN PATENT DOCUMENTS

| | | |
|---|---|---|
| CN | 105127442 A | 12/2015 |
| CN | 107446264 A | 12/2017 |

(Continued)

OTHER PUBLICATIONS

Sakai, H. et al., "Preparation of Highly Dispersed Core/Shell-type Titania Nanoparticles Containing a Single Ag Nanoparticle", J. American Chemical Society, vol. 128, pp. 4944-4945, published on Web Mar. 23, 2006.*

Nadagouda, M.N. et al., "Green synthesis of silver and palladium nanoparticles at room temeperature using coffee and tea extract", Green Chemistry, vol. 10, pp. 859-862, published on Web Jul. 1, 2008.*

(Continued)

*Primary Examiner* — George Wyszomierski
(74) *Attorney, Agent, or Firm* — Oblon, McClelland, Maier & Neustadt, L.L.P.

(57) ABSTRACT

An efficient green method for the synthesis of noble metal/transition metal oxide nanocomposite comprising reducing noble metal salt and a templating metal oxide is disclosed. The method is a one-step method comprises mixing coffee seed husk extract, a noble metal precursor, and a transition metal precursor; and filtering and drying the nanocomposite. The nanocomposite prepared by the method of the invention displays all the characteristics and biocidal activity of a composite prepared by traditional methods.

11 Claims, 17 Drawing Sheets

(56) References Cited

U.S. PATENT DOCUMENTS

| | | | | |
|---|---|---|---|---|
| 2007/0128439 A1* | 6/2007 | Kim | ............... | B82Y 30/00 |
| | | | | 428/404 |
| 2010/0166870 A1* | 7/2010 | Iyer | ............... | B01J 2/14 |
| | | | | 424/490 |
| 2010/0200501 A1* | 8/2010 | Hoag | ............... | B82Y 30/00 |
| | | | | 210/620 |
| 2014/0106260 A1* | 4/2014 | Cargnello | ............... | B01J 35/0013 |
| | | | | 429/528 |
| 2016/0081347 A1 | 3/2016 | Niedermeyer | | |
| 2018/0355191 A1* | 12/2018 | Ueda | ............... | B22F 1/02 |

FOREIGN PATENT DOCUMENTS

| | | |
|---|---|---|
| CN | 104472543 B | 6/2018 |
| EP | 2 887 936 B1 | 3/2016 |

OTHER PUBLICATIONS

Dhand, et al.; Green synthesis of silver nanoparticles using Coffea arabica seed extract and its antibacterial activity; Materials Science and Engineering C 58; pp. 36-43; Aug. 15, 2015; 9 Pages.

Yu, et al.; The antifungal efficacy of nano-metals supported TiO and ozone on the resistant Aspergillus niger spore; Journal of Hazardous Materials vol. 261; pp. 155-162; Oct. 15, 2013; Abstract Only; 2 Pages.

Boxi, et al.; Ag doped hollow TiO nanoparticles as an effective green fungicide against Fusarium solani and Venturia inaequalis phytopathogens; Nanotechnology vol. 27, No. 8; Jan. 25, 2016; Abstract Only; 2 Pages.

\* cited by examiner 100 nm

GREEN SYNTHESIS OF NOBLE METAL/TRANSITION METAL OXIDE NANOCOMPOSITE

BACKGROUND OF THE INVENTION

Field of the Disclosure

The invention pertains to a method for green synthesis of photocatalyst nanocomposites comprising a noble metal, a metal oxide, and reduced graphene oxide, compositions containing the photocatalyst nanocomposites, heterojunction structures based on the photocatalyst nanocomposites, and methods of purifying water using the photocatalyst nanocomposites for photodecomposition of soluble organic contaminants by sunlight.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

Nanotechnology is a rapidly growing field with potential application in fields ranging from electronics to cosmetics [Kamat, P. V. "Photophysical, photochemical and photocatalytic aspects of metal nanoparticles" J. Phys. Chem. B 106 (2002) 7729-7744; and Manikprabhu et al. "Synthesis of silver nanoparticles using *Streptomyces coelicolor* klmp33 pigment: an antimicrobial agent against extended-spectrum beta-lactamase (ESBL) producing *Escherichia coli*" Mater. Sci. Eng. C 45 (2014) 434-437]. Nanoscience covers the basic understanding of physical, chemical, and biological properties of nanoparticles [Adams et al. "Nanoscience, nanotechnology and spectrometry" Spectrochim Acta B 86 (2013) 3-13]. It has opened the doors for rapidly growing technologies involving the design and development of novel materials which exhibit unique and improved properties. Silver nanoparticles (SNPs) have wide range of commercial applications in several fields such as optics, electronics, catalysis, sensors and therapeutics [Shukla et al. "Synthesis and characterization of agar based silver nanoparticles and nanocomposite film with antibacterial applications" Bioresour. Technol. 107 (2012) 295-300; Som et al. "Nano silver:antimony glass hybrid nanocomposites and their enhanced fluorescence application" Solid State Sci. 13 (2011) 887-895; and Janardhanan et al. "Synthesis and surface chemistry of nano silver particles" Polyhedron 28 (2009) 2522-2530]. Currently, they are used in a variety of products such as, but not limited to silver nanoparticles infused food storage containers [Echegoyen et al. "Nanoparticle release from nano-silver antimicrobial food containers, Food Chem. Toxicol. 62 (2013) 16-22], medical devices coated with silver nanoparticles to reduce nosocomial infections, bandages, footwear, and countless household items [Rai et al "Silver nanoparticles as a new generation of antimicrobials, Biotechnol" Adv. 27 (2009) 76-83]. According to Ayurveda, an ancient Indian medical essay, silver nanoparticles are popular additive in several Indian health products due to their unique ability to fight infectious diseases [Pal et al "The ancient Indian nanomedicine" J. Adv. Pharm. Technol. Res. 5 (2014) 4-12; Chaudhary, A. "Ayurvedic bhasma: nanomedicine of ancient India-its global contemporary perspective" J. Biomed. Nanotechnol. 7 (1) (February 2011) 68-69; Sanjoy, K. P. "The Ayurvedic Bhasma: The Ancient Science of Nanomedicine, Recent Pat. Nanomed. 5 (2015) 12-18; and H. Panda, H. Handbook "On Ayurvedic Medicines with Formulae, Processes and Their Uses" ISBN: 978-81-86623-63-3 2004, p. 10]. On the other hand, SNPs are gaining more importance in the medical field as antimicrobial agents, diagnostic tools, and detecting biomolecules. The large surface area of SNPs allows them to have a better contact with microorganisms and thus, impart good antibacterial activity even at lower concentrations. When SNPs penetrate a cell of a microorganism, the particle releases silver ions, and thereby killing the microorganism. Several mechanisms have been proposed to explain the biocidal activity of silver ion or SNPs on bacteria such as: i) inactivation of respiratory chain, ii) disruption of cell membrane and leakage of its cellular contents, iii) binding to functional group of proteins causing protein denaturation and cell death, iv) inhibiting DNA replication, and v) denaturation of enzymes which transport nutrients across bacterial cell membrane [Kumar et al. "Highly efficient Ag/C catalyst prepared by electro-chemical deposition method in controlling microorganisms in water" J. Mol. Catal. A 223 (2004) 313-319]. Thus, silver nanoparticles are effective biocidal agent against a broad spectrum of gram-negative and gram-positive bacteria, including the antibiotic resistant strains [Mohanty et al. "An investigation on the antibacterial, cytotoxic, and antibiofilm efficacy of starch-stabilized silver nanoparticles" Nanomedicine: NBM 8 (2012) 916-924].

SNPs can be synthesized by various methods such as but not limited to reduction reaction, chemical and photochemical reactions, thermal decomposition, radiation assisted methods, and electrochemical processes as well as sonochemical and microwave assisted synthesis [Janardhanan et al. "Synthesis and surface chemistry of nano silver particles" Polyhedron 28 (2009) 2522-2530; Shinde et al. "A green synthesis method for large area silver thin film containing nanoparticles, J. Photochem. Photobiol. B 136 (2014) 19-25; Bankura et al. "Synthesis, characterization and antimicrobial activity of dextran stabilized silver nanoparticles in aqueous medium" Carbohydr. Polym. 89 (2012) 1159-1165; and Kathiravan et al. "Synthesis of silver nanoparticles from *Melia dubia* leaf extract and their in vitro anticancer activity, Spectrochim. Acta A 130 (2014) 116-121]. Although these methods can successfully produce silver nanoparticles, they usually involve the use of toxic and hazardous chemicals which have several harmful effects on the environment and human health [Rani et al. "Green synthesis of silver-protein (core-shell) nanoparticles using Piper betle L. leaf extract and its eco-toxicological studies on *Daphnia magna*, Colloids Surf. A 389 (2011) 188-194]. Also, the final product requires additional purification steps, as some of the byproducts of the method are adsorbed on the surface of SNPs, which may have undesired effects in certain applications. In addition, current methods in use for preparing SNPs utilize expensive chemicals, which usually contain stabilizers to prevent agglomeration of SNPs. On the other hand, green chemistry is a widely accepted alternative process for synthesizing SNPs.

Green synthesis does not involve the use of any toxic chemicals as it is efficient, cost-effective, and environment friendly, and does not require any stabilizer. Various environmental friendly materials including plant extracts, bacteria, actinomycetes, fungi, and enzymes are considered green reagents and have been used successfully in green syntheses. SNPs synthesized by green process are highly compatible for pharmaceutical and other biomedical applications [Tagad et al. "Green synthesis of silver nanoparticles and their application for the development of optical fiber based hydrogen peroxide sensor" Sensors Actuators B Chem. 183 (2013) 144-149]. The process can be easily scaled up for the bulk synthesis of SNPs without involving the use of any high pressure and/or temperature [Mittal et al. "Synthesis of metallic nanoparticles using plant extracts, Biotechnol. Adv. 31 (2013) 346-356]. Various plant materials have been explored by researchers to synthesize silver nanoparticles [Shinde et al. Kathiravan et al.; Rani et al.; Tagad et al.; Mittal et al.; Vijayaraghavan et al. "Biomimetic synthesis of silver nanoparticles by aqueous extract of Syzygium *aromaticum*" Mater. Lett. 75 (2012) 33-35; Venkateswarlu et al. "A novel green synthesis of $Fe_3O_4$—Ag core shell recyclable nanoparticles using *Vitis vinifera* stem extract and its enhanced antibacterial performance" Physica B 457 (2015) 30-35; and Rao et al. "Green synthesis and spectral characterization of silver nanoparticles from Lakshmi tulasi (*Ocimum* sanctum) leaf extract" Spectrochim. Acta A 103 (2013) 156-159]. The key phytochemicals responsible for converting silver ions into silver nanoparticles are terpenoids, glycosides, alkaloids, flavonoids, coumarins, ubiquinones, tannins, and the like as identified by IR spectroscopic studies [Mariselvam et al. "Green synthesis of silver nanoparticles from the extract of the inflorescence of *Cocos nucifera* (Family: Arecaceae) for enhanced antibacterial activity" Spectrochim. Acta A 129 (2014) 537-541; and Krishnaraj et al. "Synthesis of silver nanoparticles using Acalypha indica leaf extracts and its antibacterial activity against water borne pathogens, Colloids Surf. B 76 (2010) 50-56]. One of the most common plant products used for daily consumption is coffee seeds of *Coffea Arabica*, i.e., coffee beans, which are known to contain high levels of phenolic compounds [Mariselvam et al. and Krishnaraj et al.].

Both CN105127442A and Dhand et al. [Mat. Sci. Engin. C (2016) 58, 36043] disclose a method of preparing silver nanoparticles using green coffee bean extract and roasted coffee bean extract, respectively, as a reducing agents. The methods comprise mixing an aqueous silver salt solution with the coffee bean extract. Dhand et al reported that the reduction reaction was followed by observing the change of color from light to dark brown, and demonstrated the antibacterial activity of the prepared silver nanoparticles on *Escherichia coli* and *Streptomyces aureus*.

CN107446264A discloses a method of making antibacterial and mold-proof film comprising polyvinyl chloride, silver loaded on titanium dioxide, epoxy soybean oil, plasticizer, and stabilizing agent. The method of the CN107446264A patent utilizes many chemical compounds, is time consuming and environmentally unfriendly.

Yu et al. [J. Hazad. Mat. (2013) 261, 155-162] discloses that nanoparticles of silver, copper, and nickel supported on titanium dioxide have antifungal activity, in particular against *Aspergillus niger*. The supported nanoparticles were prepared by an incipient wetness method using commercial titanium dioxide obtained from Degussa-Evonik, Also, they further reported that the critical silver concentration required to inhibit the germination of *A. niger* spores is 65 mg/mL. Yu et al. do not disclose any synthetic methods of the nanoparticles.

Boxi et al. [Nanotechnology (2016) 27, https://doi.org/10.1088/0957-4484/27/8/085103] disclose the potent antifungal activity of silver doped solid and hollow titanium dioxide nanoparticles. The hollow nanoparticles were shown to have higher antifungal activity and to be effective in protecting potatoes from infection by *Fusarium solani*.

While the above prior art utilized plant material extract as a reducing reagent for the preparation of silver nanoparticles, the plant materials utilized in the methods have ecological and/or commercial value, e.g., coffee beans or plants parts required for the survival of the plant. It is therefore one object of the invention is to provide a green method for the synthesis of metal nanoparticles utilizing waste materials such as coffee bean husks.

The foregoing paragraphs have been provided by way of general introduction, and are not intended to limit the scope of the following claims. The described embodiments, together with further advantages, will be best understood by reference to the following detailed description taken in conjunction with the accompanying drawings.

SUMMARY

One aspect of the invention is directed to a method of preparing noble metal nanoparticles comprises adding an aqueous coffee seed husk extract (CSHE) to an aqueous solution of noble metal salt to form a transition metal nanoparticle suspension.

In a preferred embodiment, the noble metal is silver, palladium, platinum, gold, ruthenium, rhodium, osmium, or iridium.

In another preferred embodiment, the noble metal precursor is a metal chloride, bromide, iodide, nitrate, or acetate.

Another aspect of the invention is directed to a method of preparing a nanocomposite comprising noble metal nanoparticles and transition metal oxide comprises adding an aqueous coffee seed husk extract (CSHE) to an aqueous solution of noble metal precursor to form noble metal nanoparticles suspension, mixing a transition metal oxide precursor with the transition metal nanoparticles suspension to form a noble metal/transition metal oxide nanocomposite.

In a preferred embodiment, the nanocomposite comprises noble metal in an amount in the range of 2 wt. % to 40 wt. %.

In another preferred embodiment, the noble metal is silver, palladium, platinum, gold, ruthenium, rhodium, osmium, or iridium.

In another preferred embodiment, the noble metal precursor is a noble metal salt.

In another preferred embodiment, the noble metal salt is a noble metal chloride, bromide, iodide, nitrate, acetate, or nitrate.

In another preferred embodiment, the noble metal precursor is silver nitrate.

In another preferred embodiment, the transition metal oxide is zinc oxide, titanium oxide, iron oxide, cobalt oxide, nickel oxide, zirconium oxide, niobium oxide or molybdenum oxide.

In another preferred embodiment, the metal oxide precursor is a transition metal alkoxide, chloride, bromide, iodide, or acetate.

In another preferred embodiment, the nanocomposite comprises silver and titanium oxide or zinc oxide.

In another preferred embodiment, the noble metal precursor is silver nitrate and the transition metal oxide precursor is titanium tetraisopropoxide.

Another aspect of the invention is directed to a method of preparing a reducing agent comprises washing a seed husk, drying and grinding the seed husk to form a powder, adding the powder to water to form a mixture, heating the mixture at a temperature in the range of 70–100° C. for a time in the range of 10-60 min, and filtering out the solid to obtain the reducing agent.

In a preferred embodiment, the seed husk is *Coffea arabica* or *Coffea canephoraseed* husk.

In another preferred embodiment, the solvent is water, alcohol, or combination thereof.

In another preferred embodiment, the alcohol is selected from the group consisting of methanol, ethanol, propanol, isopropanol, butanol, and isobutanol.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1A:
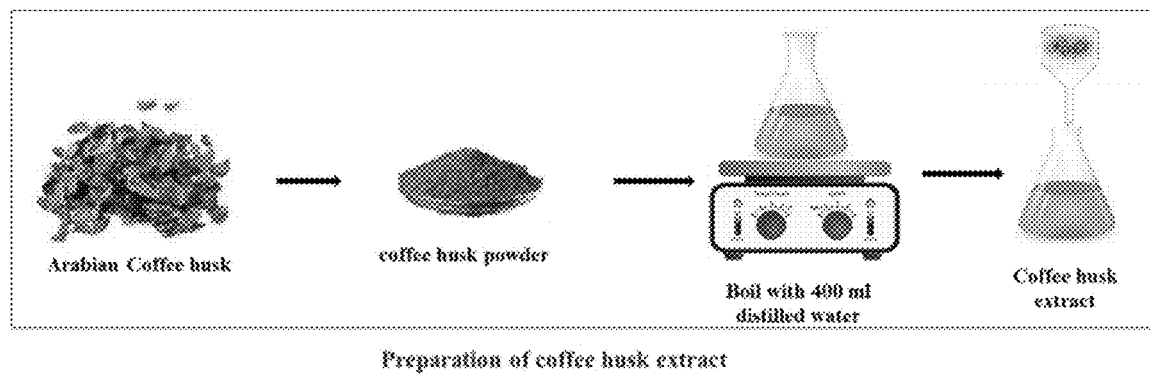
FIG. 1A shows a method of making coffee seed husk extract.

Embodiments of the present disclosure will now be described more fully hereinafter with reference to the accompanying drawings, in which some, but not all embodiments of the disclosure are shown. The present disclosure will be better understood with reference to the following definitions.

All publications mentioned herein are incorporated herein by reference in full for the purpose of describing and disclosing the methodologies, which are described in the publications, which might be used in connection with the description herein. Nothing herein is to be construed as an admission that the inventors are not entitled to antedate such disclosure by virtue of prior disclosure. Also, the use of "or" means "and/or" unless stated otherwise. Similarly, "comprise," "comprises," "comprising" "include," "includes," and "including" are interchangeable and not intended to be limiting.

Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

As used herein, the term "compound" is intended to refer to a chemical entity, whether in a solid, liquid or gaseous phase, and whether in a crude mixture or purified and isolated.

As used herein, the term "salt" refers to derivatives of the disclosed compounds, monomers or polymers wherein the parent compound is modified by making acid or base salts thereof. Exemplary salts include, but are not limited to, mineral or organic acid salts of basic groups such as amines, and alkali or organic salts of acidic groups such as carboxylic acids. The salts of the present disclosure can be synthesized from the parent compound that contains a basic or acidic moiety by conventional chemical methods. Generally such salts can be prepared by reacting the free acid or base forms of these compounds with a stoichiometric amount of the appropriate base or acid in water or in an organic solvent, or in a mixture of the two; generally non-aqueous media like ether, ethyl acetate, ethanol, isopropanol, or acetonitrile are preferred.

As used herein, the term "about" refers to an approximate number within 20% of a stated value, preferably within 15% of a stated value, more preferably within 10% of a stated value, and most preferably within 5% of a stated value. For example, if a stated value is about 8.0, the value may vary in the range of 8±1.6, ±1.0, ±0.8, ±0.5, ±0.4, ±0.3, ±0.2, or ±0.1.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

The method of the invention utilizes an extract of waste plant materials as a reducing material. Many waste plant material comprises several organic compounds such as, but not limited to polyphenol, quinic acid, vanilic acid, ferulic acid, chlorogenic acid, caffeic acid, tannin, lignine, and caffeine, which may act alone or in combinations as reducing agent for noble metal salts. As used herein, the term "waste plant material" referrer to a byproduct of processing plants product such as seed husk, dry leaves, branches, wood cuttings, and the like. Such products ordinarily have no economic value and are usually discarded or burned.

The seed husk used in the method of the invention may be any husk of any plant seed such as, but not limited to rice, wheat, corn, coffee, soy, and barley. In some embodiments, the husk is of a seed of a plant belong to the genus *Cofea*, which is a genus of flowering plants in the family Rubiaceae.

*Coffea* species are shrubs or small trees native to tropical and southern Africa and tropical Asia. The seeds of some species, called coffee beans, are used to flavor various beverages and products. The fruits, like the seeds, contain a large amount of caffeine, and have a distinct sweet taste and are often juiced. The plant ranks as one of the world's most valuable and widely traded commodity crops and is an important export product of several countries, including those in Central and South America, the Caribbean and Africa. There are over 120 species of *Coffea*, which is grown from seed. The two most popular are *Coffea arabica*, commonly known as "*Arabica*" and *Coffea canephora*, known as "*Robusta*". *Arabica* accounts for 60-80% of the world's coffee production and *Robusta* accounts for about 20-40%. As such, a considerable amount of coffee seed husks are produced as a byproduct of processing coffee beans. In some embodiments of the invention, the husk is obtained from *Coffea arabica* or *Coffea canephora*.

In some embodiments of the present disclosure, the waste plant material is coffee seed husk, in particular, *Coffea arabica* or *Coffea canephora* seed husk. The husk is the outer layer of the coffee bean that breaks away and is discarded during the roasting process. Large quantities of coffee seed husk are produced every day after roasting coffee beans. An extract may be prepared by adding ground dry husk to a solvent and optionally heating it, e.g., heating to the boiling point of the solvent, for a time in the range of 0.1-3 h, preferably 0.2-2.5 h, preferably 0.3-2 h, preferably 0.4-1 h, preferably about 0.5 h. The solvent may be water, alcohol such methanol, ethanol, propanol, isopropanol, butanol, isobutanol, and the like, ether such as dimethyl ether, methyl ethyl ether, diethyl ether, halogenated hydrocarbons such as methylene chloride, chloroform, carbon tetrachloride, and the like, acetone, acetonitrile, and the like. In a preferred embodiment of the method, the solvent is water and the extract is prepared by boiling an amount of dried and comminuted coffee been husk in the range of 1-10 wt. %, preferably 2-9 wt. %, preferably 3-8 wt. %, preferably 4-7 wt. %, preferably 4.5-5.5 wt. % for about 0.5 h.

The method of the invention comprises mixing a solution of a noble metal precursor with the coffee husk extract described herein for a time in the range of 1-48 h, preferably 2-24 h, preferably 3-15 h, preferably 4-12 h, preferably 5-10 h. As used herein, the term "noble metal" is a metal selected from the group consisting of ruthenium (Ru), rhodium (Rh), palladium (Pd), silver (Ag), osmium (Os), iridium (Ir), platinum (Pt), and gold (Au). As used herein the word "diameter" refers to the average diameter of a nanoparticle measured by transmission electron microscopy (TEM). The nanoparticles may contain nanoparticles of one or more of the noble metals such that the nanoparticles have a diameter in the range of 1-999 nm, preferably, 20-500 nm, preferably 30-100 nm, preferably 40-80 nm, preferably 50-70 nm, preferably 55-60 nm. In some embodiments of the invention, the noble metal nanoparticles are silver or gold having a diameter in the range of 5 nm to 100 nm, preferably, 10 nm to 80, preferably 20 nm to 60 nm, preferably 30 nm to 50 nm, preferably 35 nm to 45 nm. The noble metal precursor may be any salt or compound of a noble metal such as but not limited to $AuF_3$, $AuF_5$, $(AuCl_3)_2$, $Au_4Cl_8$, $AuBr$, $AuBr_3$, $AuI$, $AuI_3$, $Au_2O_3$, $Au_2S$, $Au_2S_3$, $HAuCl_4$, $PtCl_2$, $PtCl_4$, $PtF_4$, $PtO_2$, $H_2PtCl_6$, palladium halide including but not limited to $PdF_2$, $PdF_3$, $PdF_4$, $PdF_6$, $Pd(PdF_6)$, palladium acetate, palladium acetylacetonate, $PdCl_2$, $PdBr_2$, palladium cyanide, $Pd(NO_3)_2$, $Ag_2CO_3$, $AgF_2$, $AgNO_3$, silver acetate, $OsO_4$, $OsO_2$, $RuO_2$, $RuO_4$, $K_2RuO_4$, $RuCl_3$, $RuF_3$, $RhCl_3$, $RhF_6$, $RhO_2$, $Na_2RhO_3$, $IrO_2$, $Ir_2O_3$, $IrO_4$, $IrCl_2$, $IrCl_3$, and the like.

The noble metal nanoparticle may be separated from the reaction mixture by filtration or centrifugation. In some embodiments, the product may be calcined to remove any remnant of organic material at a temperature of at least 150°

C., preferably 200° C., preferably 250° C., preferably 300° C., preferably 350° C., preferably 400° C. for a time in the range of 2-12 h, preferably 4-10 h, preferably 5-6 h.

Another aspect of the invention is directed to a method of making a nanocomposite of a noble metal nanoparticle supported on a transition metal oxide that is similar to the method described herein above for making noble metal nanoparticles. The method comprises mixing a solution of noble metal precursor with the coffee husk extract as described herein above to form a suspension of noble metal nanoparticle in coffee husk extract. To the suspension, a solution of a transition metal oxide precursor is mixed with agitation and the mixture is allowed to stand for of 1-48 h, preferably 2-24 h, preferably 3-15 h, preferably 4-12 h, preferably 5-10 h.

The amount of noble metal in the nanocomposite is in the range of 1 wt. % to 30 wt. %, preferably 2 wt. % to 25 wt. %, preferably of 5 wt. % to 20 wt. %, preferably 8 wt. % to 15 wt. % of the total weight of the nanocomposite.

The transition metal oxide nanoparticles have a diameter in the range of 20 nm to 500 nm, preferably 30 nm to 250 nm, preferably 50 nm to 100 nm, preferably 60 nm to 80 nm. The transition metal oxide is an oxide of an element such as, but not limited to, Sc, Ti, V, Cr, Mn, Fe, Co, Ni, Zn, Y, Zr, Nb, and Mo. In some preferred embodiments of the invention, the metal oxide is selected from the group consisting of Zn, V, Cr, Mn, Fe, Co, and Ni. Preferably the metal oxide is that of Ti. Titanium dioxide, also known as titanium(IV) oxide or titania, is a naturally occurring oxide of titanium.

Any suitable metal salt such as that of, but not limited to, Sc, Ti, V, Cr, Mn, Fe, Co, Ni, Zn, Y, Zr, Nb, and Mo may be utilized. Examples of the salts include, but are not limited to halides, carboxylate, carbonate, alkoxide and the like such as, but not limited to $ZnCl_2$, $ZnBr_2$, zinc acetate, zinc isopropoxide, $Zn(OCH_3)_2$, titanium isopropoxide, $ZrCl_4$, $Zr_4(OC_2H_5)_{16}$, $FeCl_2$, $FeCl_3$, $TiCl_4$, $Ti_4(OC_2H_5)_{16}$, titanium tetraisopropoxide, $VCl_3$, $VBr_3$, vanadium acetate, vanadium oxytriisopropoxide, $MnCl_2$, $MnBr_2$, manganese acetate, and the like.

In some embodiments, the mixture may be heated at a temperature in the range of 100-200° C., preferably in the range of 110-180° C., preferably in the range of 120-160° C., preferably at about 150° C. for a time in the range of 10 to 20 hours for a time in the range of 10 to 20 hours for a time in the range of 5 to 30 hours, preferably in the range of 10 to 25 hours, preferably, about 15 hours. The noble metal nanoparticles or nanocomposite are filtered, washed, and dried at a temperature in the range of 50-120° C., preferably 60-100° C., and preferably 70-80° C. In some embodiments, the nanocomposite product may be calcined to remove any remnant of organic material at a temperature of at least 150° C., preferably 200° C., preferably 250° C., preferably 300° C., preferably 350° C., preferably 400° C. for a time in the range of 2-12 h, preferably 4-10 h, preferably 5-6 h, preferably about 3 h.

One of the advantages of the method of the invention is that it produces highly porous metal oxide nanoparticles. The highly porous nanoparticles are templated by some of the components of coffee seed husk extracts. The high porosity of the metal oxide of the composite makes it suitable for use in many applications including, but not limited to catalysis, electrochemical applications, and adsorption.

Another aspect of the invention is directed to a method of preparing a reducing agent comprising washing a seed husk, drying and grinding the seed husk to form a powder, adding the powder to a solvent to form a mixture, heating the mixture at a temperature in the range of 70-100° C. for a time in the range of 10-60 min, and filtering away the solid to obtain the reducing agent. Any solvent may be use in the method such as but not limited to water, ethanol, methanol, propanol, isopropanol, butanol, isobutanol, pentane, cyclopentane, hexane, cyclohexane, acetone, diemthyl ether, diethyl ether, acetonitrile, dimethylformamide, chloroform, methylene chloride, carbontetrachloride and combination thereof.

The husk used in the method of the invention may be any husk of any plant seed such as, but not limited to rice, wheat, corn, coffee, soy, and barley. In some embodiments, the husk is of a seed of a plant belong to the genus *Cofea*, in particular, *Coffea arabica* or *Coffea canephora* as large amounts of husk produced every day from processing coffee beans. In a particular embodiment, the method mixing water and a dry ground husk powder of seed husk from *Coffea arabica* or *Coffea canephora* and heating the mixture to a temperature in the range of 70–100° C., preferably 80-100° C., preferably 90-100° C., preferably 95-100° C. for a time in the range of 10-120 min, preferably 10-80 min, preferably 20-60 min, preferably 30-40 min. The amount of powder is in the range of 1-15 wt. %, preferably 2-13 wt. %, preferably 3-12 wt. %, preferably 4-10 wt. %, preferably 5-8 wt. % of the total weight Example 1

Preparation of Coffee Seed Husk Extract (CSHE):

The coffee husks were washed several times with distilled water to remove the dust particles on their surface then air dried. The dried husk was grinded to obtain fine powder. Coffee husk powder (20 g) was boiled with 400 ml of distilled water for 30 min, then allowed to cool down slightly and finally filtered to obtain clear brown solution of CSHE (see FIG. 1A).

Table 1 provides a qualitative comparison of various components in coffee husk and coffee beans.

TABLE 1

| Chemical compounds in Coffee Husk | Chemical compounds in Coffee Been |
| --- | --- |
| Caffeine (low level) | Caffeine (high level) |
| Tannin | Tannin (high level) |
| Lignin | — |
| Cellulose | NA |
| Hemicellulose | NA |
| Caffeic acid (low level) | Caffeic acid (high level) |
| Chlorogenic acid (low level) | Chlorogenic acid (high level) |
| Ferulic acid | Ferulic acid |
| Vanillic acid | NA |
| quinic acid | NA |
| Polyphenols | Polyphenols |

[1] Andrade et al. "Supercritical fluid extraction from spent coffee grounds and coffee husks: Antioxidant activity and effect of operational variables on extract composition" *Talanta*, vol. 88, pp. 544-552 (2012);
[2] United Kingdom "P & A- 084 In Vitro Antioxidant Activity of Coffee Compounds and Their" no. Ldl, pp. 6962-6969 (2007);
[3] Dhand et al. "Green synthesis of silver nanoparticles using *Coffea arabica* seed extract and its antibacterial activity" *Mater. Sci. Eng. C*, vol. 58, pp. 36-43 (2016);
[4] Louarn et al. "Caffeine, trigonelline, chlorogenic acids and sucrose diversity in wild *Coffea arabica* L. and *C. canephora* P. accessions" *Food Chem.*, vol. 75, no. 2, pp. 223-230 (2001);
[5] Mohan et al. "Biotechnological potential of coffee pulp and coffee husk for bioprocesses" *Biochem. Eng. J.*, vol. 6, pp. 153-162 (2002);
[6] Brand et al. "Biological detoxification of coffee husk by filamentous fungi using a solid state fermentation system" *Enzyme Microb. Technol.*, vol. 27, no. 1-2, pp. 127-133 (2000);
[7] Mussatto et al. "Production, Composition, and Application of Coffee and Its Industrial Residues" *Food Bioprocess Technol.*, vol. 4, no. 5, pp. 661-672 (2011);
[8] Castaldo et al. "Study of the Chemical Components Bioactivity and Antifungal Properties of the Coffee Husk" *J. Food Res.*, vol. 7, no. 4, p. 43 (2018);
[9] Al-Yousef et al. "Essential oil of *Coffee arabica* L. Husks: A brilliant source of antimicrobial and antioxidant agents" *Biomed. Res.*, vol. 29, no. 1, pp. 174-180 (2018),
[10] Campos-Vega et al. "Spent coffee grounds: A review on current research and future prospects" *Trends Food Sci. Technol.*, vol. 45, no. 1, pp. 24-36 (2015);
[11] Mazzafera, P. "Degradation of caffeine by microorganisms and potential use of decaffeinated coffee husk and pulp in animal feeding" *Sci. Agric.*, vol. 59, no. 4, pp. 815-821, (2005); and
[12] Oliveira and A. S. Franca, *An Overview of the Potential Uses for Coffee Husks*. Elsevier Inc. (2014) - each incorporated by reference.

Example 2

Figure 1B:
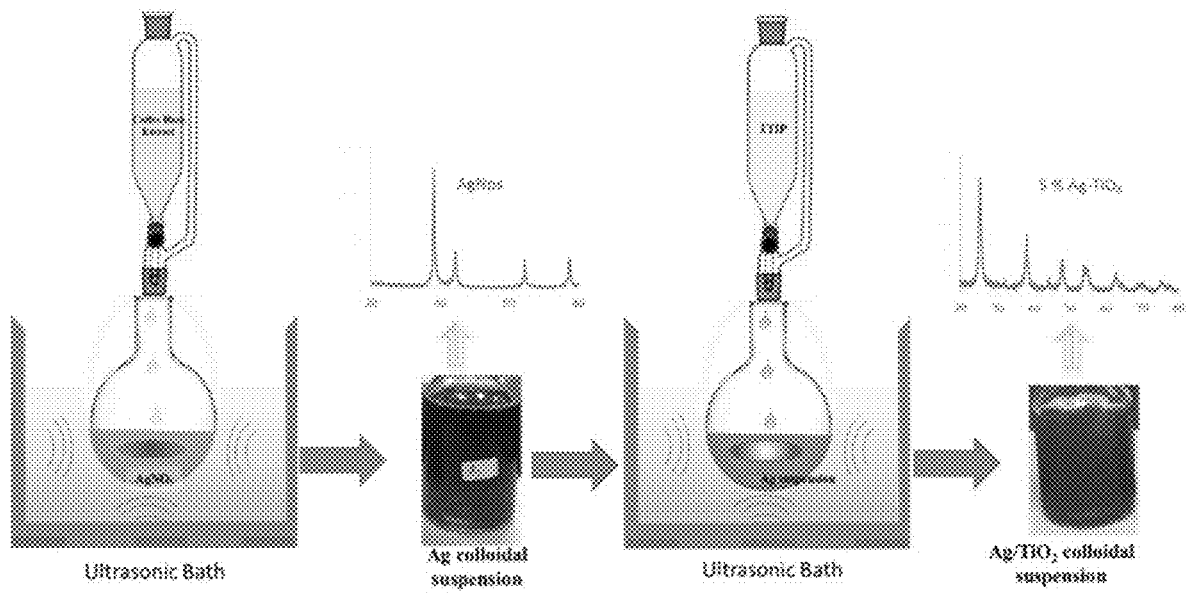
FIG. 1B shows a schematic representation of preparing M/TiO$_2$ using coffee seed husk extract.
Figure 1C:
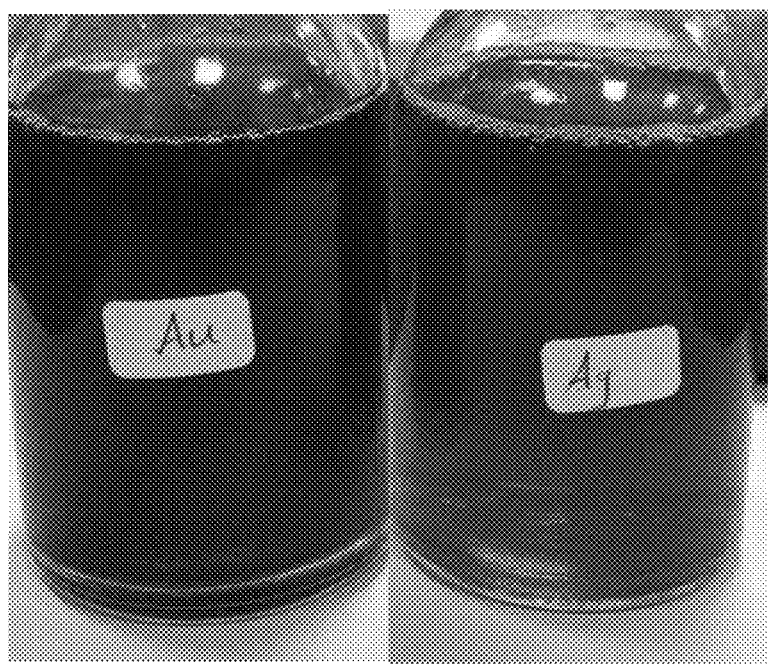
FIG. 1C shows colloidal suspensions of Au and Ag nanoparticles prepared using coffee seed husk extract.

Preparation of Silver Nanoparticles and Nanocomposite:

Silver nanoparticles were prepared by dropwise addition of CSHE on an aqueous solution of silver nitrate agitated with ultrasound to form silver nanoparticles. Ag—$TiO_2$ nanocomposite was prepared by dropwise addition of an aqueous solution of titanium tetraisopropoxide to a solution containing the desired amount of silver nanoparticles and CSHE with agitation at ambient temperature (see FIGS. 1B and 1C). The resulting precipitate was filtered, washed with deionized water, dried, and calcined at 300° C. for one hour to produce porous nanocomposite of Ag—$TiO_2$. The same procedure was used to obtain $TiO_2$ from titanium tetraisopropoxide and gold nanoparticles from gold salt (see FIG. 1C).

Figure 11A:
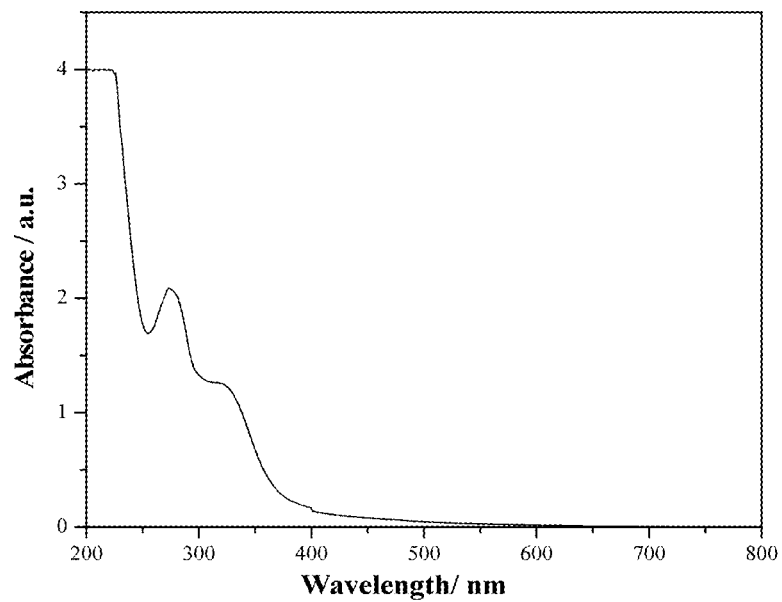
FIG. 11A shows a UV-vis spectrum of the Coffee Husk Extract (CHE)
Figure 11B:
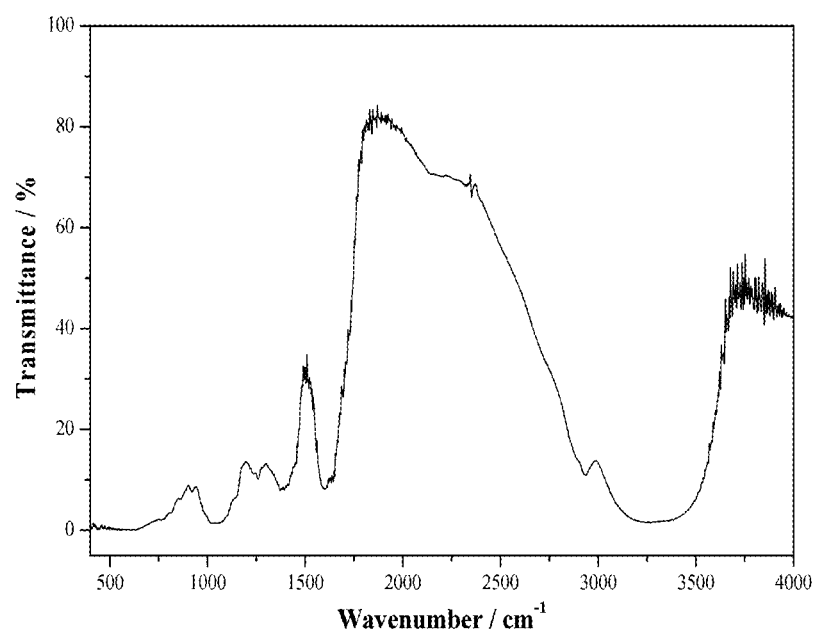
FIG. 11B shows an FTIR of the Coffee Husk Extract (CHE).

Characterization of the Nanocomposite:

Crystalline structure, morphology and optical properties of the produced green nanomaterials and nanocomposites have been examined by XRD, UV-vis diffuse reflectance spectroscopy, and FTIR spectroscopy. The results show that the green prepared nanomaterials are pure and have high crystallinity and modified size and shape with narrow particle distribution as compared to the corresponding nanomaterials prepared by chemical methods. The nanomaterials have meso porous/macro porous channels with 1.37-1.5 μm interior width which are well arranged, particle size ranged from 8 to 10 nm. FTIR and UV-Vis spectra of FIGS. 11B and 11A, respectively, reveal that phenolic compounds are present in CSHE and act efficiently as reducing and templating/stabilizing agents during synthesis process. The FTIR spectra of the obtained CSHE shows broad absorption peak from 3600 to 3200 $cm^{-1}$ which can be assigned to an —OH group of polyphenolic compounds. The absorption at 1700 $cm^{-1}$ corresponds to the carbonyl stretching vibration of free caffeine. A peak at 1655 $cm^{-1}$ of vs (CO)+v (CC) in free caffeine. The Quadratal CN stretching in imidazole ring appearing at 1403 $cm^{-1}$ of the caffeine. The vibrations of free caffeine appearing at 2900, 1700, 1683, 1456 and the broad bands at 1284-973, 925 $cm^{-1}$.

CHE was further analyzed by UV-vis absorption spectroscopy measurement (FIG. 11A) with absorption in the range 200-400 nm. Two peaks were observed, one peak at 275 nm is attributed to caffeine and the peak at 320 nm is attributed to Caffeic acid. The results indicate the presence of polyphenolic, Caffeic acid and Caffeine which act as bio-templating agents for the synthesis of the porous $TiO_2$ nanoparticles. [See U. T. C. P. Souto, M. F. Barbosa, H. V. Dantas, A. S. Pontes, W. S. Lyra, P. H. G. D. Diniz, M. C. U. Araújo, E. CSilva, *Food Science and Technology*, 2015, 63, 1037-1041, and Diding Suhandy & Meinilwita Yulia, *International Journal of Food Properties*, 2017, 20, S331-S339—each incorporated by reference].

Figure 12A:
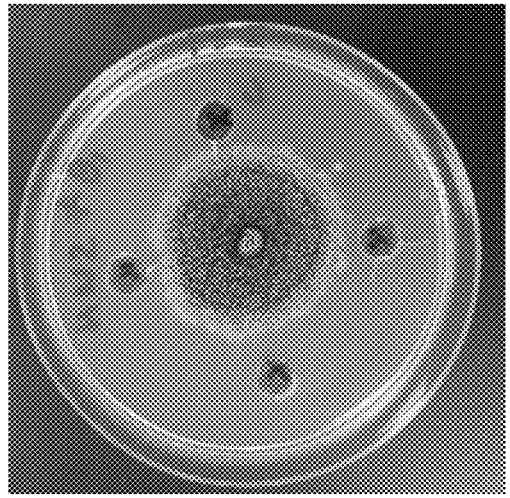
FIG. 12A shows the antifungal activity of Ag/TiO$_2$ nanocomposites with 1% Ag concentration.
Figure 12B:
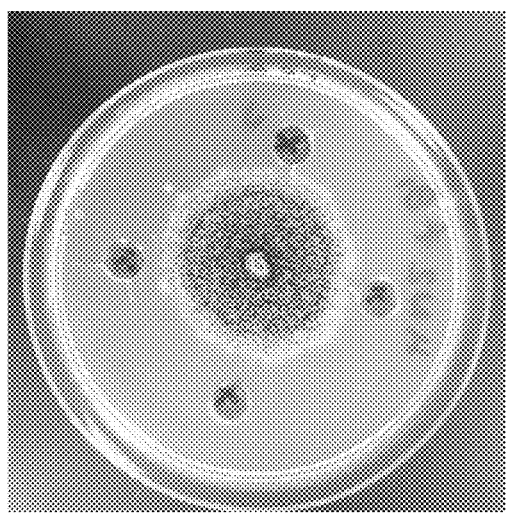
FIG. 12B shows the antifungal activity of Ag/TiO$_2$ nanocomposites with 5% Ag concentration.
Figure 12C:
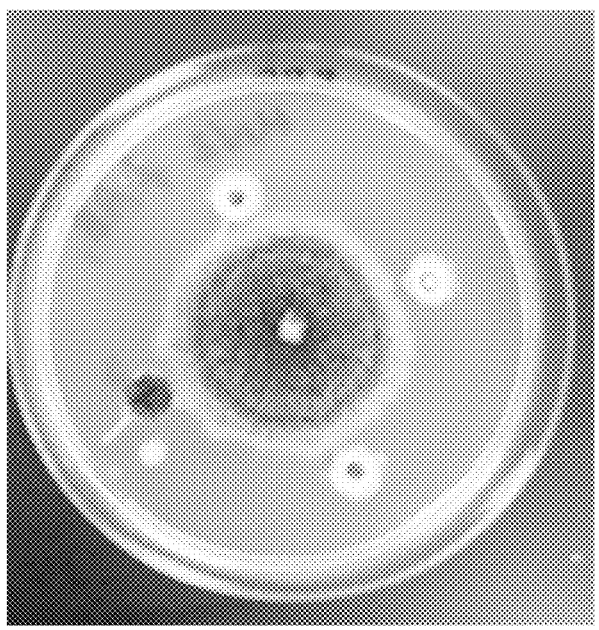
FIG. 12C shows the antifungal activity of Ag/TiO$_2$ nanocomposites with 10% Ag concentration.

The effect of the ratio of Ag nanoparticles in the nanocomposite was studied. It was found that no noticeable change in the antifungal activity was observed among various Ag/$TiO_2$ samples with various Ag ratios (see FIGS. 12A, 12B and 12C).

Figure 2A:
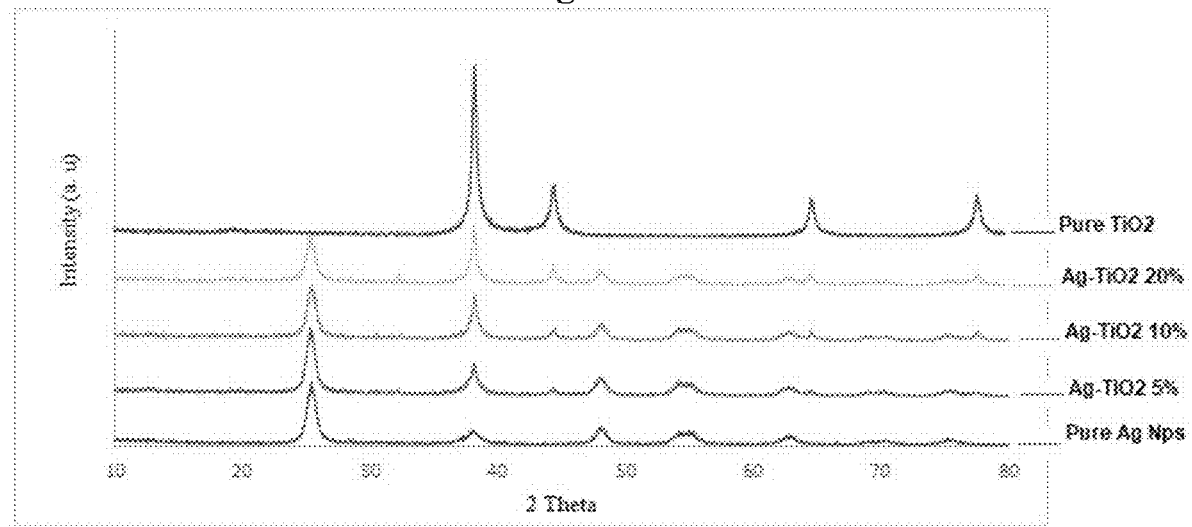
FIG. 2A shows XRD patterns of green Ag nanoparticles, TiO$_2$ nanoparticles and Ag—TiO$_2$ nanocomposites of various Ag ratios.
Figure 2B:
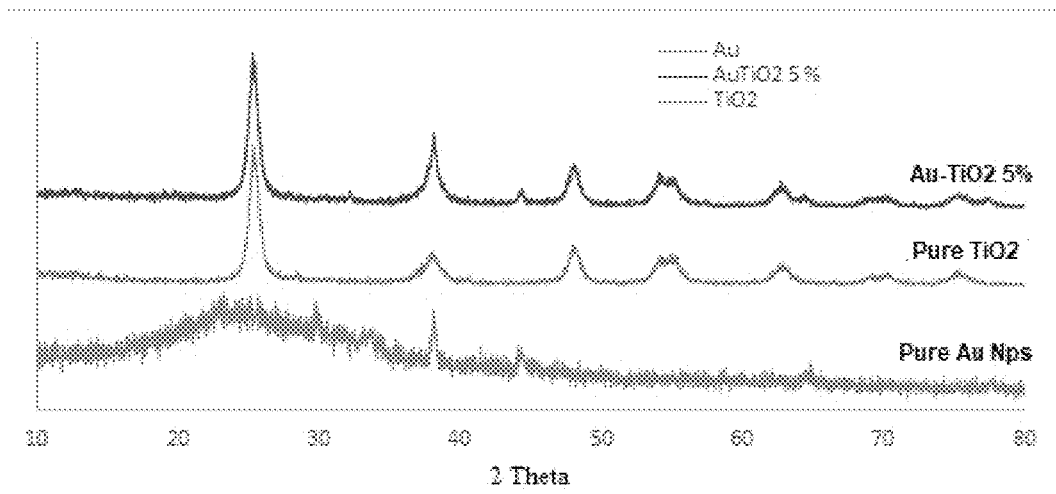
FIG. 2B shows XRD patterns of green Au nanoparticles, TiO$_2$ nanoparticles and 5% Au—TiO$_2$ nanocomposite.

FIG. 2A shows XRD patterns of the as prepared green Ag, $TiO_2$ nanoparticles, and Ag—$TiO_2$ nanocomposites having 5 wt. %, 10 wt. %. and 20 wt. % of Ag of the total weight of the composite. FIG. 2B shows XRD of Au, $TiO_2$, and composite of 5% Au/$TiO_2$.

Figure 3:
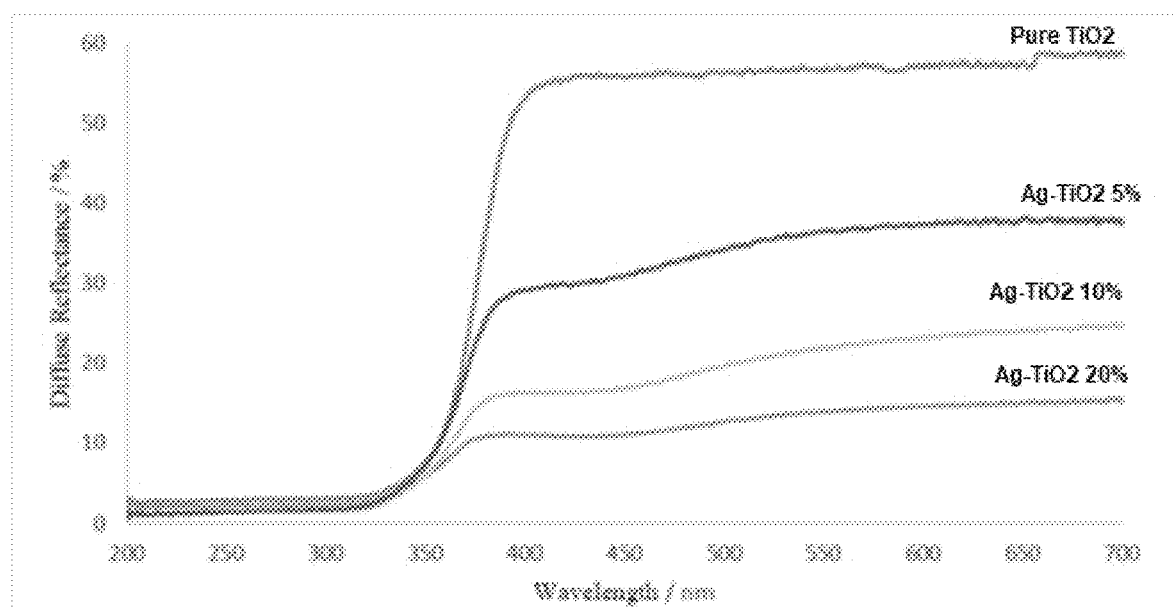
FIG. 3 shows UV-vis diffuse reflectance spectra of the as prepared green TiO$_2$ nanoparticles and Ag—TiO$_2$ nanocomposites having 5 wt. %, 10 wt. %. and 20 wt. % of Ag of the total weight of the composite.

FIG. 3 shows UV-vis diffuse reflectance spectra of the as prepared green $TiO_2$ nanoparticles and Ag—$TiO_2$ nanocomposites having 5 wt. %, 10 wt. %. and 20 wt. % of Ag of the total weight of the composite.

Figure 4:
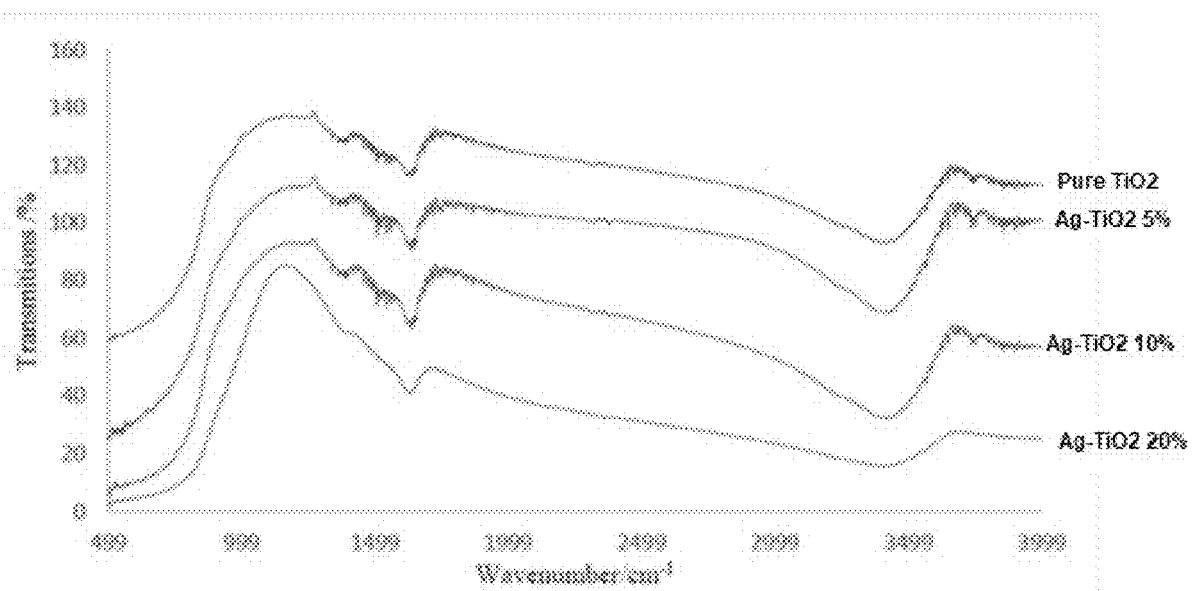
FIG. 4 shows FTIR spectra of the as prepared green TiO$_2$ nanoparticles and Ag—TiO$_2$ nanocomposites having 5 wt. %, 10 wt. %. and 20 wt. % of Ag of the total weight of the composite.

FIG. 4 shows FTIR spectra of the as prepared green $TiO_2$ nanoparticles and Ag—$TiO_2$ nanocomposites having 5 wt. %, 10 wt. %. and 20 wt. % of Ag of the total weight of the composite.

Figure 5A:
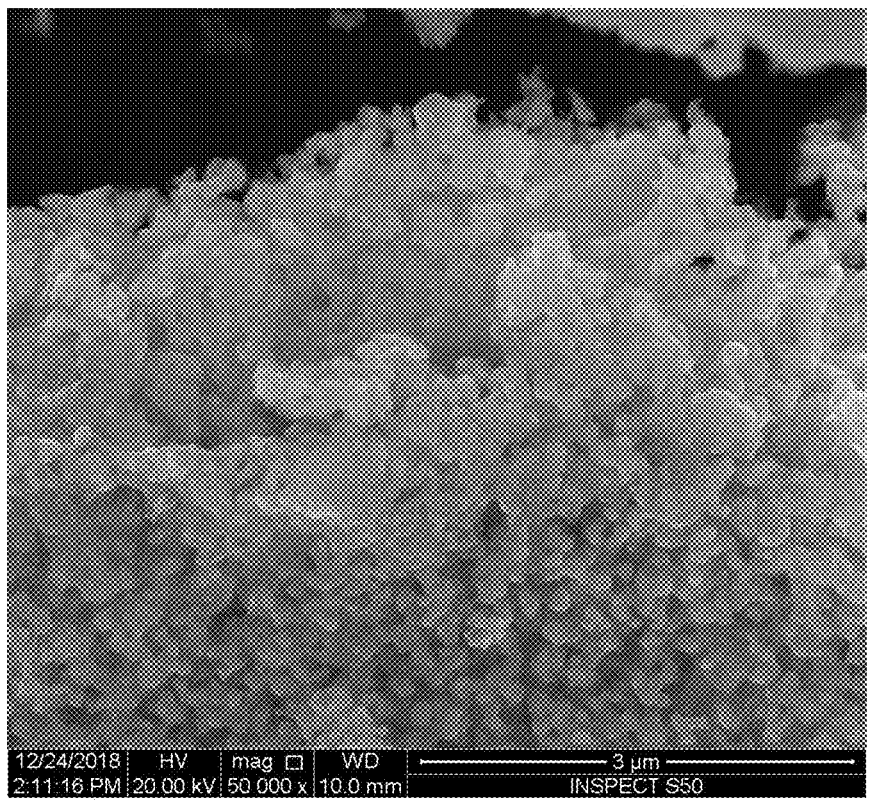
FIG. 5A shows SEM image of Ag nanoparticles.
Figure 5B:
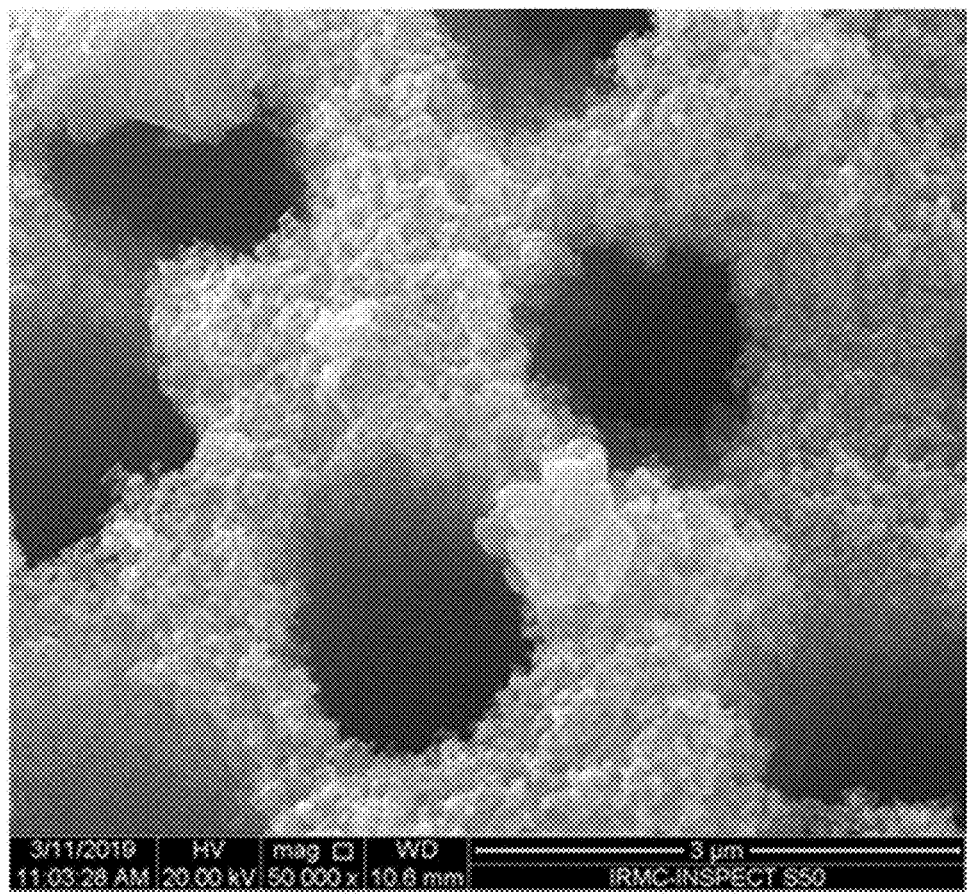
FIG. 5B shows SEM image of Ag/TiO$_2$ nanocomposite.

FIGS. 5A and 5B show the SEM images of Ag nanoparticles and 5% Ag/$TiO_2$ nanocomposite, respectively, prepared by the method of invention.

Figure 6A:
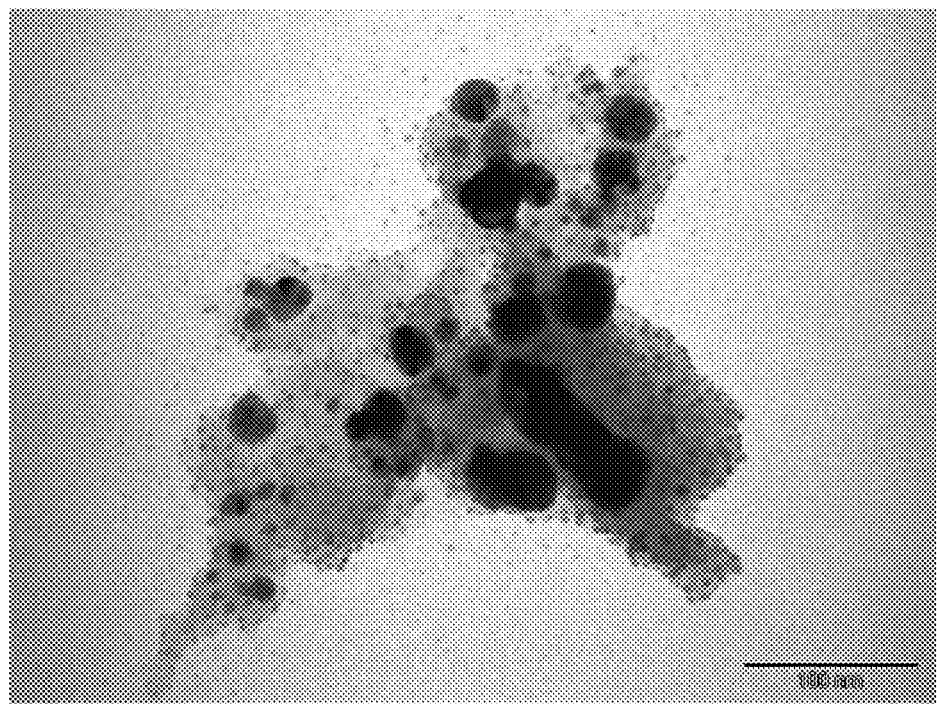
FIG. 6A shows TEM image of Ag nanoparticles synthesized by the green method.
Figure 6B:
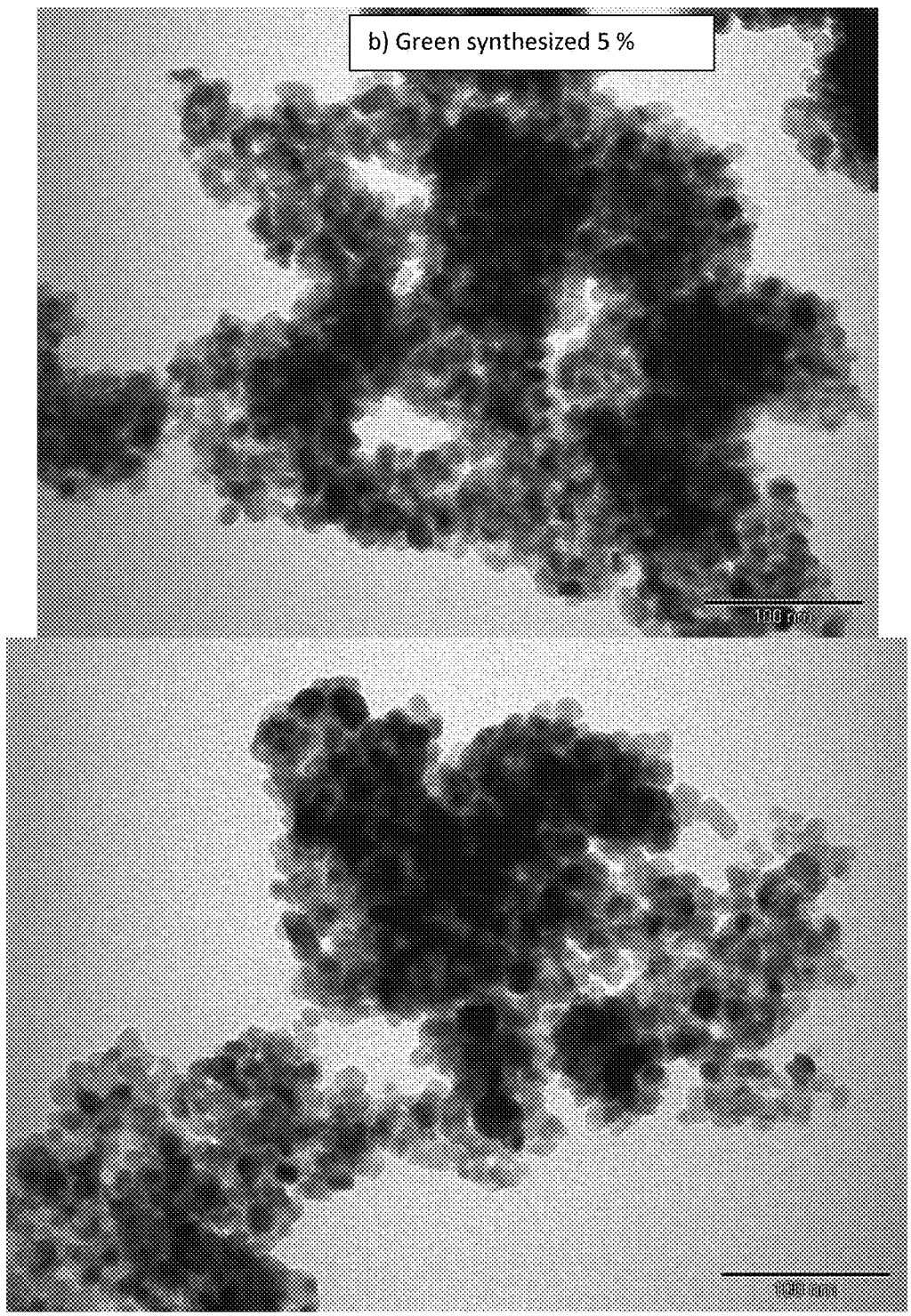
FIG. 6B shows TEM image of 5% Ag/TiO$_2$ nanocomposite synthesized by the green method at 1× magnification.
Figure 6C:
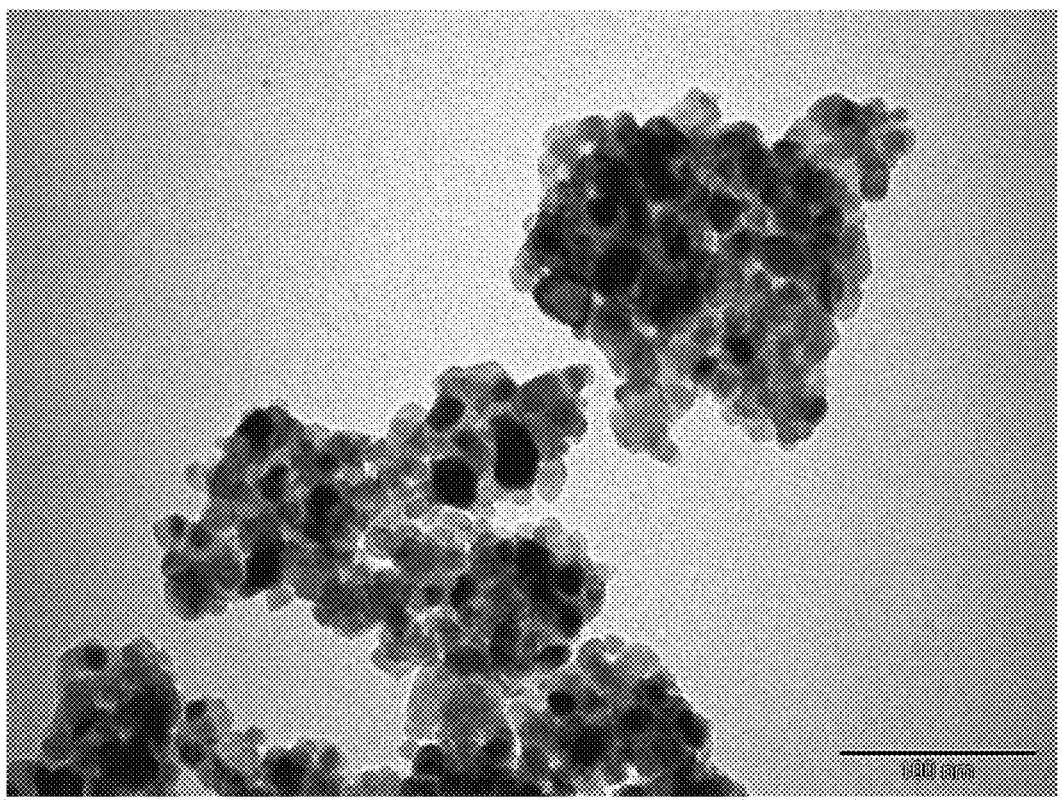
FIG. 6C shows TEM image of 5% Ag/TiO$_2$ nanocomposite synthesized by a chemical method.
Figure 7A:
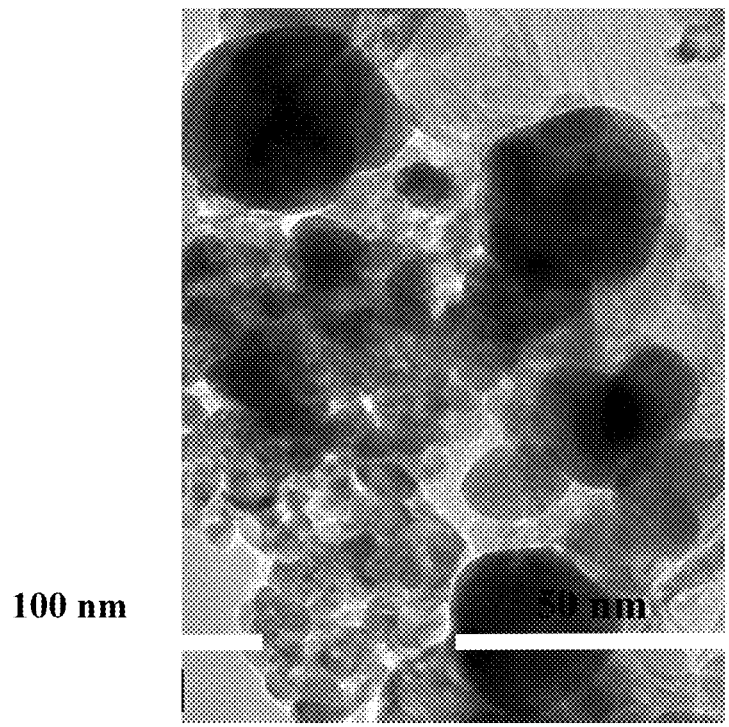
FIG. 7A shows TEM image of 5% Ag/TiO$_2$ nanocomposite synthesized by the green method at 4× magnification.
Figure 7B:
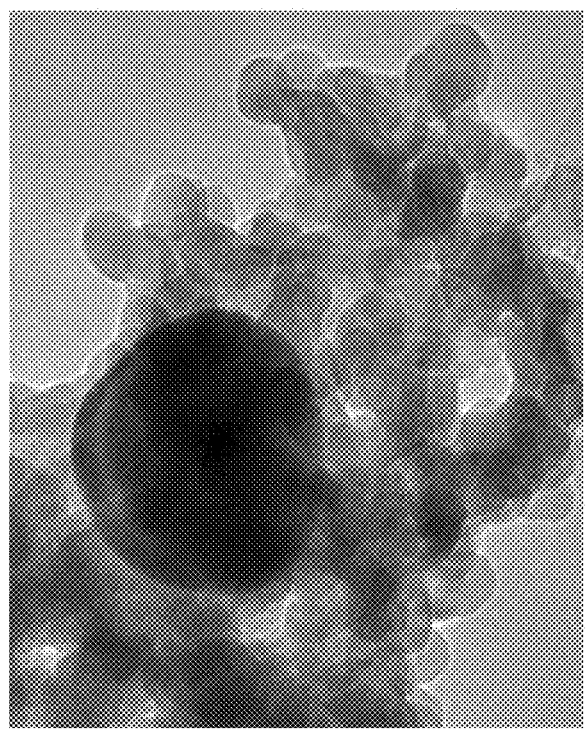
FIG. 7B shows TEM image of 5% Ag/TiO$_2$ nanocomposite synthesized by the green method at 8× magnification.

FIG. 6A shows a TEM image of Ag nanoparticles prepared by the method of invention. FIGS. 6B and 6C show the TEM image of 5% Ag/$TiO_2$ nanocomposite, respectively, prepared by the method of invention and by conventional method, respectively, at 1× magnification. FIGS. 7A and 7B show TEM images at 4× and 8× magnification, respectively.

Example 3

Figure 8A:
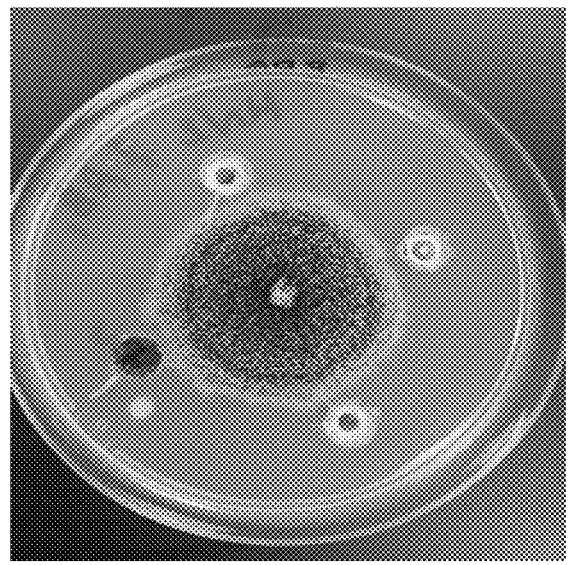
FIG. 8A shows the growth of *Aspergillus niger* on an agar well containing Ag/TiO$_2$ nanocomposite at the center of the plate.
Figure 8B:
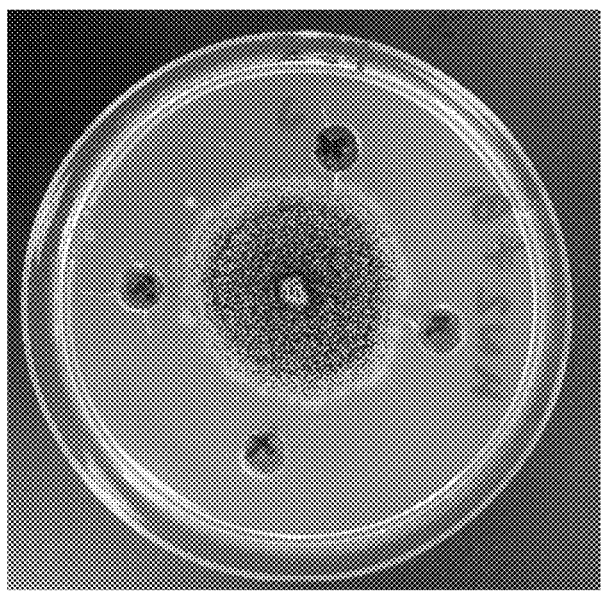
FIG. 8B shows the growth of *Aspergillus niger* on an agar well containing Ag nanoparticles at the center of the plate.
Figure 10:
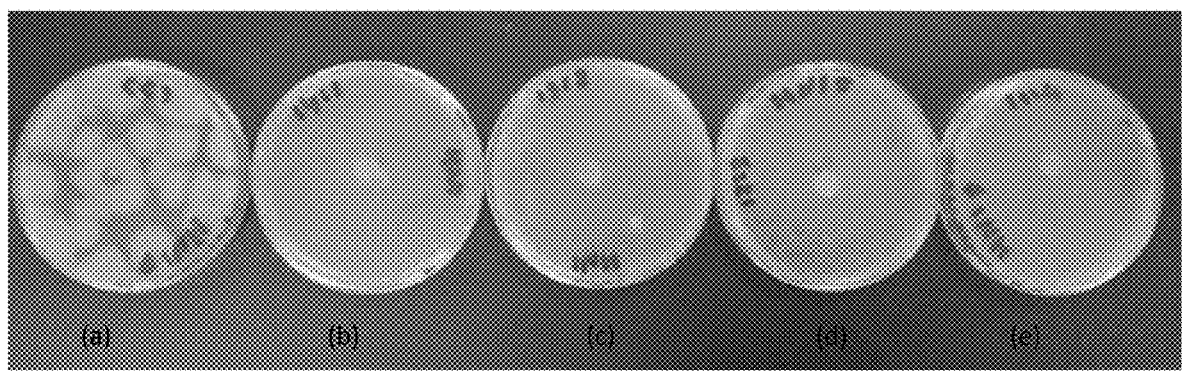
FIG. 10 shows the effects of the green synthesized 5 mmol % Ag—TiO$_2$ nanocomposites on radial growth of fungi. (a) Control sample, (b-e) at concentrations of 1, 2, 3, 4 mg/ml of Ag—TiO$_2$ nanocomposite from left to right, respectively.

Biocidal Activity of the Nanoparticles:

The biocidal activity of the nanoparticles and nanocomposites prepared by the method of invention were examined by the agar well diffusion method in cultures of *Aspergillus flavus* and *Aspergillus niger*. Different concentrations of Ag and Ag/$TiO_2$ nanocomposite were added to 90 ml of molten potato dextrose agar, pH 6. PDA petri plates without any nanoparticles and nanocomposite were incubated as a control. All plates were inoculated in the center with 6 mm diameter fungal disc. All the plates were incubated at room temperature 28±2° C. for 4 days. The growth of the fungal pathogen in treated plates was measured when the growth of the organism in control plate was full (FIGS. 8A and 8B). Each experiment was repeated thrice and the average values were recorded. The presence of clearance zone indicates the high fungal sensitivity to Ag/$TiO_2$ nanocomposite more than Ag nanoparticles. The negative control (water) had no effect on the tested fungi (plate (a) in FIG. 10 in which the concentration of the nanocomposite used in experiments b-e was in the following order: 1 mg/ml, 2 mg/ml, 3 mg/ml, 4 mg/ml].

Ag/$TiO_2$ and Ag inhibited the growth of tested fungi and the results are summarized in Tables 1-3.

TABLE 1

Antifungal activity of Ag and Ag/$TiO_2$ against *Aspergillus niger* and *Aspergillus flavus*.

| Fungal strains | Treatment with Ag | | | | | Treatment with Ag/$TiO_2$ | | | | |
|---|---|---|---|---|---|---|---|---|---|---|
| | 0.5 mg/ml | 1 mg/ml | 2 mg/ml | 3 mg/ml | 4 mg/ml | 0.5 mg/ml | 1 mg/ml | 2 mg/ml | 3 mg/ml | 4 mg/ml |
| | | | | | Inhibition zones (mm) | | | | | |
| A. niger | 13 ± 0.43 | 14.5 ± 0.23 | 15 ± 0.32 | 16.5 ± 0.35 | 16.5 ± 0.3 | 13.5 ± 0.30 | 15 ± 0.33 | 16 ± 0.25 | 17 ± 0.33 | 20 ± 0.45 |
| A. flavus | 14 ± 0.65 | 15.5 ± 0.25 | 16 ± 0.25 | 17.5 ± 0.35 | 17.5 ± 0.2 | 17 ± 0.30 | 19 ± 0.5 | 18.75 ± 0.25 | 19 ± 0.32 | 19 ± 0.35 |

TABLE 2

| | Percentage of radial growth inhibition* | | | | | | | | |
|---|---|---|---|---|---|---|---|---|---|
| | Treatment with Ag | | | | | Treatment with Ag/TiO₂ | | | |
| Fungal strains | 0.5 mg/ml | 1 mg/ml | 2 mg/ml | 3 mg/ml | 4 mg/ml | 0.5 mg/ml | 1 mg/ml | 2 mg/ml | 3 mg/ml | 4 mg/ml |
| | | | | | Mycelium growth inhibition (%) | | | | |
| A. niger | 68 ± 3.5 | 87 ± 2.5 | 100 | 100 | 100 | 65 ± 2.5 | 82 ± 2.8 | 100 | 100 | 100 |
| A. flavus | 76 ± 4 | 94 ± 3.3 | 100 | 100 | 100 | 100 | 100 | 100 | 100 | 100 |

*Values are given as mean ± S.D. of three experiments

TABLE 3

Minimum Inhibitory concentration (MIC) and MFC values recorded against *Aspergillus flavus* and *Aspergillus niger*
Treatment (mg/ml)

| | Ag/TiO₂ | | Flucanazole* | |
|---|---|---|---|---|
| Fungi | MIC | MFC | MIC | MFC |
| A. flavus | 0.2 | 0.35 | 0.1 | 0.1 |
| A. niger | 0.5 | 1 | 0.1 | 0.1 |

*Antigoni Elefanti, Johan W. Mouton, Katerina Krompa, Rafal Al-Saigh, Paul E. Verweij, Loukia Zerva, and Joseph Meletiadis, Inhibitory and Fungicidal Effects of Antifungal Drugs against *Aspergillus* species in the presence of serum, Antimicrob Agents Chemother. 2013 April; 57(4): 1625-1631. doi: 10.1128/AAC.01573-12. MFC: Minimum Fungicidal Concentration with concentration in mg/ml.

Figure 9A:
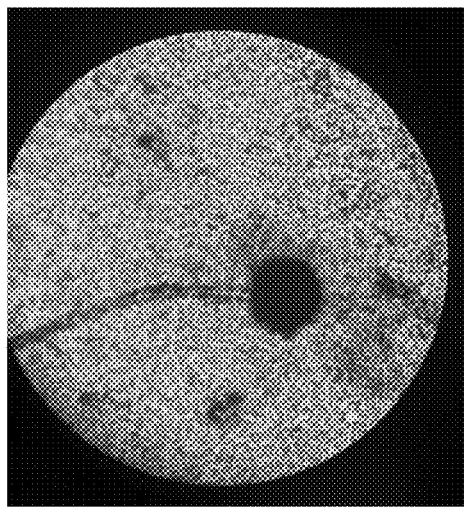
FIG. 9A shows an optical micrograph of control mycelia of *Aspergillus niger*.
Figure 9B:
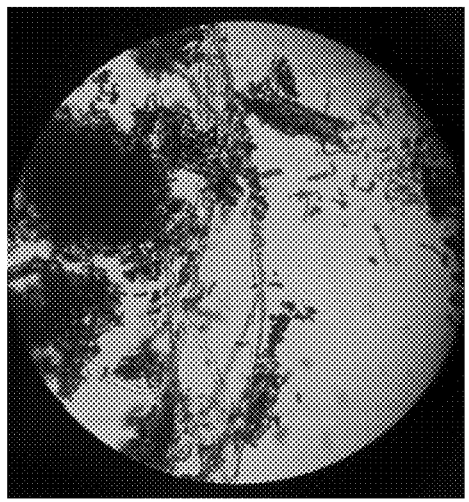
FIG. 9B shows an optical micrograph of mycelia of *Aspergillus niger* treat with Ag/TiO$_2$.

The maximum growth inhibition of *A. flavus* was observed at concentration of 1 mg/mL of Ag/TiO₂ nanocomposite and 3 mg/ml of Ag nanoparticles. In case of *A. niger*, Ag/TiO₂ inhibited completely the growth at concentration of 3 mg/ml, while Ag completely inhibited the growth at concentration of 4 mg/ml. For the two strains, the inhibition is irreversible. Thus, the growth sensitivity of *Aspergillus* strains to Ag/TiO₂ nanocomposite and Ag nanoparticles was species dependent and concentrations dependent in the case of *Aspergillus niger*. The morphology of mycelia of *Aspergillus niger* treated with Ag/TiO₂ nanocomposite was significantly altered from that intact mycelia of the control (compare FIGS. 9A and 9B).

In order to explore the impact of Ag/TiO₂ nanocomposite and Ag nanoparticles on intracellular pH level, concentrations of 1 mg/mL and 4 mg/mL of Ag/TiO₂ were tested respectively against *A. flavus* and *A. niger*. The initial pH was adjusted to pH 6. The prepared suspension was kept in a shaking incubator at speed of 200 rpm at 28° C. The pH changes in suspension were measured using pH meter. The result demonstrates that only control fungi maintain constant internal pH while treated strains shows increase in internal acidification to provide a culture acidity of pH 6. The increase was more pronounced in cultures of *A. flavus*. The result suggests that, the produced green nanomaterials exhibit antifungal activity by targeting $H^+$-ATPase located in the fungi membranes causing intracellular acidification which leads to cell death.

The invention claimed is:

1. A method of preparing a nanocomposite comprising noble metal nanoparticles and transition metal oxide, comprising:
    adding an aqueous coffee seed husk extract (CSHE) to an aqueous solution of a noble metal precursor to form a noble metal nanoparticle suspension while sonicating the aqueous solution of a noble metal precursor with ultrasound, wherein the CSHE is obtained by extracting a powder consisting of coffee seed husk,
    adding a solution of a transition metal oxide precursor to the noble metal nanoparticle suspension while sonicating the noble metal nanoparticle suspension with ultrasound to form a noble metal/transition metal oxide nanocomposite suspension,
    filtering the noble metal/transition metal oxide nanocomposite suspension to isolate a noble metal/transition metal oxide nanocomposite precursor, then
    calcining the noble metal/transition metal oxide nanocomposite precursor to form a noble metal/transition metal oxide nanocomposite, wherein the noble metal/transition metal oxide nanocomposite has meso porous/macro porous channels with an interior width of 1.37 to 1.5 μm and a particle size range of from 8 to 10 nm.

2. The method of claim 1, wherein the noble metal/transition metal oxide nanocomposite comprises a noble metal in an amount in the range of 1 wt. % to 40 wt. % based on the total weight of the noble metal/transition metal oxide nanocomposite.

3. The method of claim 1, wherein the noble metal is silver, palladium, platinum, gold, ruthenium, rhodium, osmium, or iridium.

4. The method of claim 1, wherein the noble metal precursor is a noble metal salt.

5. The method of claim 4, wherein the noble metal salt is a noble metal chloride, bromide, iodide, acetate, or nitrate.

6. The method of claim 1, wherein the noble metal precursor is silver nitrate.

7. The method of claim 1, wherein the transition metal oxide is zinc oxide, titanium oxide, iron oxide, cobalt oxide, nickel oxide, zirconium oxide, niobium oxide or molybdenum oxide.

8. The method of claim 1, wherein the transition metal oxide precursor is a transition metal alkoxide, chloride, bromide, iodide, or acetate.

9. The method of claim 1, wherein the noble metal/transition metal oxide nanocomposite comprises silver and titanium oxide or zinc oxide.

10. The method of claim 1, wherein the noble metal precursor is silver nitrate and the transition metal oxide precursor is titanium tetraisopropoxide.

11. The method of claim 1, wherein the coffee seed husk is obtained from *Coffea arabica* or *Coffea canephora*.

* * * * *